US006898290B1

(12) United States Patent
Saunders et al.

(10) Patent No.: US 6,898,290 B1
(45) Date of Patent: May 24, 2005

(54) ADAPTIVE PERSONAL ACTIVE NOISE REDUCTION SYSTEM

(75) Inventors: William Richard Saunders, Blacksburg, VA (US); Michael Allen Vaudrey, Columbia, SC (US)

(73) Assignee: Adaptive Technologies, Inc., Blacksburg, VA (US)

(*) Notice: Subject to any disclaimer, the term of this patent is extended or adjusted under 35 U.S.C. 154(b) by 0 days.

(21) Appl. No.: 09/534,731

(22) Filed: Mar. 27, 2000

Related U.S. Application Data

(62) Division of application No. 08/852,245, filed on May 6, 1997, now Pat. No. 6,078,672.

(51) Int. Cl.[7] ......................... A61F 11/06; G10K 11/16; H03B 29/00

(52) U.S. Cl. ........................ 381/71.6; 381/72; 381/71.7

(58) Field of Search ........................... 381/71.6, 72, 74, 381/73.1, 370, 371, 375, 378, 71.7, 384, 94.2, 94.3

(56) References Cited

U.S. PATENT DOCUMENTS

| | | | | |
|---|---|---|---|---|
| 3,098,121 A | | 7/1963 | Wadsworth | |
| 4,025,721 A | | 5/1977 | Graupe et al. | |
| 4,122,303 A | | 10/1978 | Chaplin et al. | |
| 4,494,074 A | | 1/1985 | Bose | |
| 4,654,871 A | | 3/1987 | Chaplin et al. | |
| 4,682,363 A | | 7/1987 | Goldfarb et al. | |
| 4,845,751 A | | 7/1989 | Schwab | |
| 4,878,188 A | | 10/1989 | Ziegler, Jr. | |
| 4,930,148 A | | 5/1990 | Lee | |
| 4,953,217 A | * | 8/1990 | Twiney et al. | 381/71.6 |
| 5,097,510 A | | 3/1992 | Graupe | |
| 5,105,377 A | | 4/1992 | Ziegler, Jr. | |
| 5,251,263 A | | 10/1993 | Andrea et al. | |
| 5,329,592 A | | 7/1994 | Altman | |
| 5,361,303 A | | 11/1994 | Eatwell | |
| 5,375,174 A | | 12/1994 | Denenberg | |
| 5,402,497 A | | 3/1995 | Nishimoto et al. | |
| 5,404,409 A | * | 4/1995 | Nagami et al. | 381/71.8 |
| 5,852,667 A | * | 12/1998 | Pan et al. | 381/71.1 |
| 5,937,070 A | * | 8/1999 | Todter et al. | 381/71.6 |
| 6,278,786 B1 | * | 8/2001 | McIntosh | 381/71.6 |
| 6,449,369 B1 | * | 9/2002 | Carme et al. | 381/71.12 |

OTHER PUBLICATIONS

"Active Noise Control Systems: Designing for the Auditory System" William R. Saunders and Michael A. Vaudrey. Proceedings of Noise–Con 96, Bellevue, Wash., Sep. 1996.

"Active Control of Sound and Vibration", by C. R. Fuller and A. R. vonFlotow, IEEE Control Systems, Dec. 1995, pp 9–19.

"A Hybrid Structural Control Approach for Narrowband and Impulsive Disturbance Rejection", by W. R. Saunders, H. H. Robertshaw and R. A. Burdisso, Noise Control Engineering Journal, Special Issue on Active Noise Control, vol. 44, No. 1, Jan.–Feb., 1996.

"Adaptive Signal Processing" Bernard Widrow & Samuel D. Stearns. Prentice–Hall Signal Processing Series. 1985 Upper Saddle River, New Jersey.

* cited by examiner

*Primary Examiner*—Xu Mei
(74) *Attorney, Agent, or Firm*—Roberts Abokhair & Mardula, LLC

(57) ABSTRACT

An improved personal noise attenuation system which attenuates both tonal and broadband sound and which includes a spatially adjustable acousto-electric sensor and attenuation means including both feedback and feed forward components so as to provide a heteronomous attenuation and more complete active noise attenuation and the adjustable acousto-electric sensor is moved to exploit the changing physical characteristics of spatial silent zones in different noise fields.

4 Claims, 12 Drawing Sheets

LIFT / RIGHT CROSS PATHS

ADAPTIVE PERSONAL ACTIVE NOISE REDUCTION SYSTEM

CROSS REFERENCE TO RELATED APPLICATIONS

This application is a divisional of U.S. application Ser. No. 08/852,245, filed May 6, 1997, now U.S. Pat. No. 6,078,672. The U.S. application Ser. No. 08/852,245 and U.S. Pat. No. 6,078,672 are each incorporated by reference herein, in their entirety, for all purposes.

BACKGROUND

This invention is related to an improved personal noise attenuation system which can be employed to attenuate noise observed by users in sound fields containing objectionable noise. The invention can be employed on headsets, silent seats and other personal applications such as an automotive radius headliner and trim package.

Most active noise control systems utilize acoustic drivers in conjunction with acoustic sensors, controller(s) and associated signal conditioning electronics to reduce preselected sound pressure levels from impinging upon the ear drum. The instant invention is in the form of a personal system which may take the form of a headset, a "silent seat"(one designed to attenuate sound pressures at the users ears when the user is occupying the chair) or other form of personal quieting system. For example, the instant system can be employed as part of the headliner in an automobile for the purpose of attenuating road, engine or other designated noise. The instant invention overcomes the current limitations of existing devices by the use of spatial adaptation of an acoustic error sensor and implementation of a unique heteronomous control algorithm. Additionally, the user has increased comfort in the headset configuration by use of non-contacting electroacoustic transducers.

The field of active noise cancellation has progressed from the simple attempts in the 1970s by Chaplin in the United Kingdom to attenuate noise to todays more complex systems which are geared to specific types of noises. The field of noise cancellation has been reviewed extensively in "Active Control of Sound" by P. A. Nelson and S. J. Elliot, Academic Press, 1991. Progress in attenuating tonal noise has included the development of digital virtual earth systems which use fewer sensors than heretofore employed (see U.S. Pat. No. 5,105,377 to Ziegler et al entitled "Digital Virtual Earth Active Cancellation System". Cancellation of unwanted broadband noise has seen development of adaptive feedforward systems which measure the noise prior to its arrival at the cancellation point. In some applications these systems have been combined to attenuate a mixture of objectionable noises. By the use of frequency domain algorithms control over the characteristics of the noise cancellation has been achieved and these algorithms have been further modified by harmonic filters in constant rate sampling of sound converting time domain signals into frequency domain signals (see U.S. Pat. No. 5,361,303 to Eatwell entitled "Frequency Domain Adaptive Control System"). Adaptive speech filters have enhanced all of the prior art attempts at noise attenuation and/or cancellation by measuring the spectrum of the data and blocking any frequencies that do not exhibit statistical properties of standard speech thereby allowing speech in noisy environments.

The use of adaptive filtering techniques is widespread today and characterized by the controller characteristics being adjusted according to an algorithm such as that disclosed by Widrow and Stearns, "Adaptive Signal Processing", Prentice Hall, 1985. Both feedback systems (see U.S. Pat. No. 4,494,074 to Bose entitled "Feedback Control") and feedforward systems (see U.S. Pat. Nos. 4,122,303 and 4,654,871, both to Chaplin and U.S. Pat. No. 4,878,188 to Ziegler)

have been used before in personal quieting systems. Adaptive filtering techniques are discussed in the patents to Graupe (has U.S. Pat. No. 5,097,510) and Graupe and et al (U.S. Pat. No. 4,025,721).

Despite the large amount of development in the personal quieting system area, the instant invention has not been conceived of by others in the field. No one heretofore has shown or described the simultaneous use of feedback and adaptive signal processing algorithms (heteronomous control) to target different features of the noise field. Nor are there any prior patents or disclosures describing the use of a spatially adaptable error microphone based on the changing dimensions of the silent zone in different noise fields.

It has been suggested to incorporate both asynchronous feedback and microphone-based feedback compensation cancellation techniques into a single system. The attenuation concept discussed by Casalli (J. G. Casalli and G. S. Robinson, "Narrow-Band Digital Active Noise Reduction include In a Siren-Cancelling Headset: Real-Ear and Acoustical Manikin Insertion Loss", Noise Control Engineering Journal, 42 (3), 1994, May/June., page 101.) but no system has been built or developed. Casalli refers to a siren-canceling headset not unlike the one described in U.S. Pat. No. 5,375,174 to Denenberg entitled "Remote Siren Headset" which is hereby incorporated by reference herein. The architecture that the article suggests is totally different from that of the instant invention and nowhere in the article does it suggest adaptive positioning of the noise microphone. There is no discussion in the article or elsewhere of using a remote microphone for a blended feedforward/feedback architecture.

There have been endless variations on the noise cancelling headset over the years including those disclosed by Wadsworth in U.S. Pat. No. 3,098,121, Chaplin et al, in U.S. Pat. No. 4,654,871, Twiney et al, in U.S. Pat. No. 4,953,217, Bourk in U.S. Pat. No. 5,182,774 and Nishimoto et al, in U.S. Pat. No. 5,402,497, all of which are hereby incorporated by reference herein. The use of circumaural headsets dominates the ANR headset market due to the lower actuator demand in the quiet enclosure afforded by earmuffs. While there are supraural headsets the instant device differentiates from them by being open-air thus affording no confinement whatsoever of the user's ears. The open air system requires controlling a higher level of sound pressure and wider variance as there is no confinement by the muffs, whether supraural or circumaural.

Various systems to affix earpieces to headgear have been proposed which those shown in U.S. patents to Altman and Goldfarb et al, U.S. Pat. Nos. 5,329,592 and 4,682,363, respectively, both of which are hereby incorporated by reference herein.

Remote control of headsets has been suggested as evidenced by U.S. Patents to Schwab and Hsiao-Chung Lee, U.S. Pat. Nos. 4,845,751 and 4,930,148, respectively.

A review of the current status of active noise control headsets illustrates the advantages of the invention. The vast majority of active noise headsets employ either feedback compensation, as in the Bose et al patent, or adaptive signal processing algorithms, as described in U.S. Pat. No. 5,375,174 to Denenberg, implemented in time domain or frequency domain format. These two distinctive architectures have unique characteristics especially in relation to one another. Feedback control relies on a compensator to maximize the sensitivity function within the stability bounds specific to the particular noise field under consideration and active noise hardware in use. This arrangement results in a reduction in the closed-loop, low frequency gain between the disturbance input (the surrounding noise field) and the output signal (the error microphone). Noise relief realized by this technique is typically between 15 to 20 dB re 20 microPa and can be achieved from approximately 50 to 700 Hz. These limitations on noise reduction and performance bandwidth cannot be overcome for reasons that are documented by experts in the active acoustic control community. In this regard see also U.S. Pat. No. 5,251,263 to Andrea et al, entitled "Adaptive Noise Cancellation and Speech Enhancement System and Apparatus Therefore".

Adaptive feedforward noise reduction for personal ANR systems has also been proposed but to a much lesser extent. Such an architecture relies on the availability of a reference signal which is correlated with the estimate of the noise field and cannot be destabilized by the control signal. Such references have been constructed for the case of periodic inputs (see Chaplin et al) such as a reciprocating pump or propeller which can be used to spawn synchronous reference signals which serve as inputs to the adaptive filter. The other approach is to provide a compensator which cancels the feedback path between a so-called controllable reference signal and the control signal, e.g., the filtered-u algorithm. The degree of noise suppression for adaptive feedforward systems is a direct function of the multiple coherence (between the constructed, or otherwise available, reference signal and the acoustic sensor which will be minimized)

$$\text{dB reduction}=20\log_{10}(1-\gamma^2)$$

The performance bandwidth is limited by the sampling frequency for the digital filter and the size of the adaptive filter but can practically achieve noise reductions into the khz range. Theoretically, this approach can provide up to 50 dB suppression of noise levels and more than triple the feedback control bandwidth of the feedback methods.

The architecture of the essential components in any personal ANR system also has profound influence on the absolute and user-perceived performance of the system. Existing active noise control headsets and systems are designed using fixed spatial separations between the electroacoustic transducers and the acoustic sensor near the listeners ear(s). Recent theoretical and experimental results have proven that the spatial dimension of the noise field reductions is a nonlinear function of the noise frequency, the electroacoustic transducer, and the separation distance between an electroacoustic transducer surface and the acoustic sensor being controlled. The silent zone spatial dimension is relatively small for typical headset components/geometries and varies with the noise frequency (FIG. 1). For a fixed frequency, the silent zone dimension varies with separation distance between the acoustic sensor and the driver (FIG. 2). This variability of the silent zone's spatial and temporal characteristics has not been properly exploited in any existing designs for personal ANR systems.

The prior art in personal ANR technology has reached an impass imposed by the tradeoffs which currently exist for the available architectures. Feedback control headsets can provide robust noise reductions, nominally 15 dB from 50 Hz to 700 Hz, but do not require the identification or generation of an uncontrollable reference signal. Adaptive feedforward headsets can achieve substantially higher noise reductions, particularly at tonal disturbances, but must have a correlated, uncontrollable reference signal available. Both types use fixed relative positioning between the electroacoustic driver, the acoustic error sensors, and the listener's eardrum. More specifically, the prior art fails to combine the features of both architectures in a single personal ANR system and fails to exploit the nonlinear dependencies of the silent zone created around by the suppression of a single error microphone. Headsets produced in the past such as the "Proactive" and "Noisebuster" headsets of Noise Cancellation Technologies, Inc. as well as those of Sennheiser, David Clark and Bose fail to contemplate the features constituting this invention.

While all the prior art discussed above relates to personal ANR systems, they are limited by lack of performance in noise fields dominated by broadband and tonal disturbances. Furthermore, they fail to optimize the perceived effectiveness, as perceived by the user, by providing real-time or psuedo real-time adaptation of the relative positioning of the ANR components. Therefore, the following invention embodies heteronomous control and adaptive spatial positioning of the ANR components, along with an open air arrangement so as to surpass the prior art in performance and comfort for the user.

SUMMARY

It is a main purpose of this invention to provide for optimal noise reduction capabilities in a personal ANR system for a variety of noise fields without compromising the wearer's comfort. By linearly combining the advantages of two diverse control algorithms, exploiting the changing physical characteristics of spatial silent zones in different noise fields and considering the user's comfort, a non-contact, fully adaptable heteronomous controlled personal ANR system becomes a major advance over the prior art. It is noteworthy that no portion of this improved system need come into contact with the user's head or ears. Normal communication remains unencumbered and the ergonomics of user comfort is no longer an issue. The system can be adapted to fit any existing headgear including formal hats, helmets, hard-hats, casual hats, sports headgear of both a protective nature as well as decorative and any other device or mechanism designed to be worn on the head or body of a user, i. e., the improved ANR system forming this invention is application independent. Since it is adapted to be selectively positioned by the user it is infinitely adaptable.

The control algorithm used herein is a heteronomous feedback/feedforward approach. The common feedback compensator is not presented as the primary means of control but rather a method for dealing with inadequacies of the adaptive feedforward algorithm thus complementing each other. The feedforward compensator method is robustly stable in the proposed architecture and thus has the capability of very high levels of noise reduction which can reach up to but not limited to 50 dB for tonals in certain cases. The controller can select the individual or combined operation of the two controllers based on the noise field measured by the suppression microphone. It is further understood that the feedback controller may be implemented in analog or digital embodiments while the feedforward filters are implemented in digital embodiments for typical noise fields but may be constructed in analog hardware for noise fields with low dimensionality.

Feedforward noise control mandates a coherent reference signal and a system identification of the transfer function existing between the controller output and the error signal terminus. Typically this is called filtered reference, filtered-u, or filtered-x algorithm, i.e., the error signal is the actual microphone signal. The control output of the algorithm is summed with the control output of the feedback controller (either digitally or with an analog summing amplifier depending on the nature of the feedback controller) and sent through the control speaker. The system identification of the control to error path for the filtered-x algorithm is done ahead of time and stored in the DSP ROM therefore eliminating the requirement for system ID.

The feedback controller is a loop shaped design which maximizes the loop gain of the controller in the frequency range of interest, typically 100 to 1000 Hz. Limitations on plant dynamics do not permit a higher frequency range to be explored. Typical feedback controllers in these devices are effected through analog hardware, which is one preferred embodiment of this controller architecture. However, the feedback controller can be included in the control software to eliminate another hardware expense. Selectivity can be manual or a frequency sensitive switch can be incorporated therein to switch the system to the most efficient mode for the type of noise being attenuated.

In accordance with this invention the arrangement of the control actuator/acoustic-electric sensor combination with respect to the subject's head offers not only comfort but several unique performance advantages. With the acoustic-electric sensor located within the radius of reverberation of the electro-acoustic actuator, the system identification used in the filtered-x version of the feedforward control remains nearly constant for relatively significant changes in the acoustic-electric sensor positions. Such an arrangement allows for an adaptable acousto-electric sensor placement to maximize the silent zone reaching the wearer's ear. A tradeoff in the size of the silent zone exists between the location of the error acoustic-electric sensor with respect to the electric-acoustic actuator (either manual or deterministically automatic) shall be adaptable for frequency dependent disturbances. This is a unique feature allowing optimal performance of this system in a given environment. In addition to adapting the position of the acoustic-electric sensors with respect to the control actuator, the control actuator is also adaptable with respect to the listener's head. This provides an added measure of comfort and performance thus allowing the user to maximize the zone of silence near the eardrum.

A primary advantage of the instant invention is its ability to reduce tonal and narrowband noises by significantly larger margins than the existing headset technologies due to the heteronomous approach. Another primary advantage is the recognition that the error microphone location is critically important to the perceived performance by the user. This phenomena is realized by the changing spatial silent zones which are created when a point pressure sensor is minimized within the radius of reverberation of a secondary speaker thus minimizing spatial spillover potential, reducing power output required of the secondary speaker, minimizing the phase delay and achievement of the highest possible stability margins for a closed loop controller.

Accordingly, it is an object of this invention to provide an ANR system which allows a wearer to maximize the zone of silence near his eardrum(s), and Another object of this invention is to provide an ANR system in which all the components are adjustable relative to the user, and It is another object of this invention to provide an ANR system with an electricacoustic sensor which is adaptable for frequency dependant disturbances, and It is yet another object of this invention to provide an ANR headset which has positionable sensors adapted to exploit the changing physical characteristics of spatial silent zones in different noise fields, and Furthermore, it is an object of this invention to provide an ANR headset with open-air sensors which do not confine the users movements or ears, and Still another object of this invention is to provide optimal noise reduction in a personal ANR headset without sacrificing wearer comfort, and Yet another object of this invention is to provide an ANR headset which is adapted to fit within a wide range of headgear worn by a user, and Another object of this invention is to provide an ANR system having an algorithmic control utilizing a feedback/feedforward heteronomous approach, and A further object of the invention involves providing an ANR system which can operate in purely feedforward mode or a feedforward combined with feedback mode, or feedback mode only.

These and other objects will become apparent when reference is had to the accompanying drawings.

DETAILED DESCRIPTION

A detailed description of all of the preferred system structures and overall intended embodiments of the adaptive personal ANR system are now explained by reference to the figures. The description commences with an explanation of the unique physics which motivate one aspect of the apparatus followed by a discussion of the various embodiments which have been conceived and/or developed for the architecture.

Figure 1:
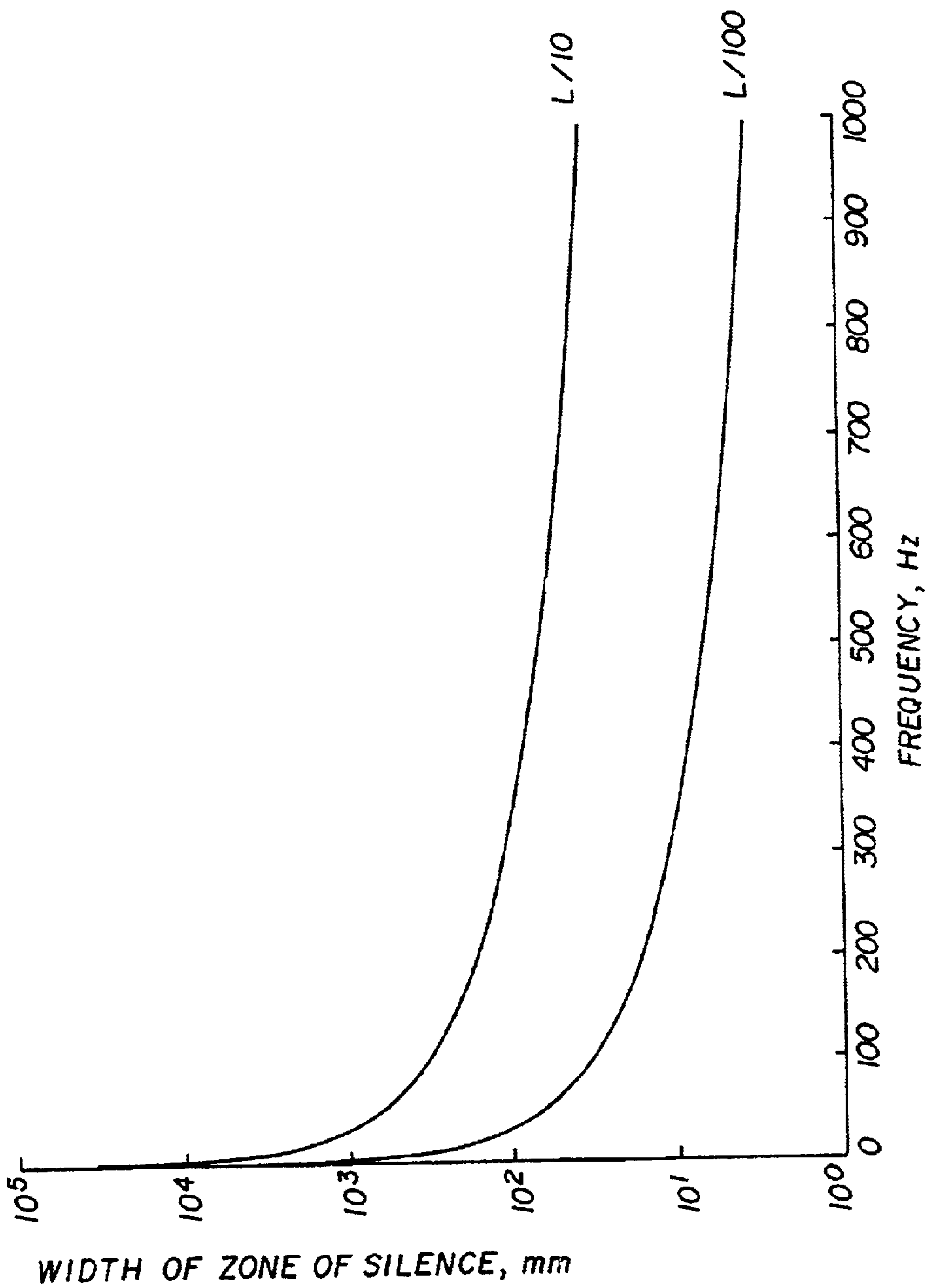
FIG. 1 is a graph plotting frequency versus width of zone of silence depicting the dimensions of the silent zone's nonlinear dependence on the frequencies suppressed by the controller for fixed electroacoustic transducer radius and microphone separation distance.
Figure 2A:
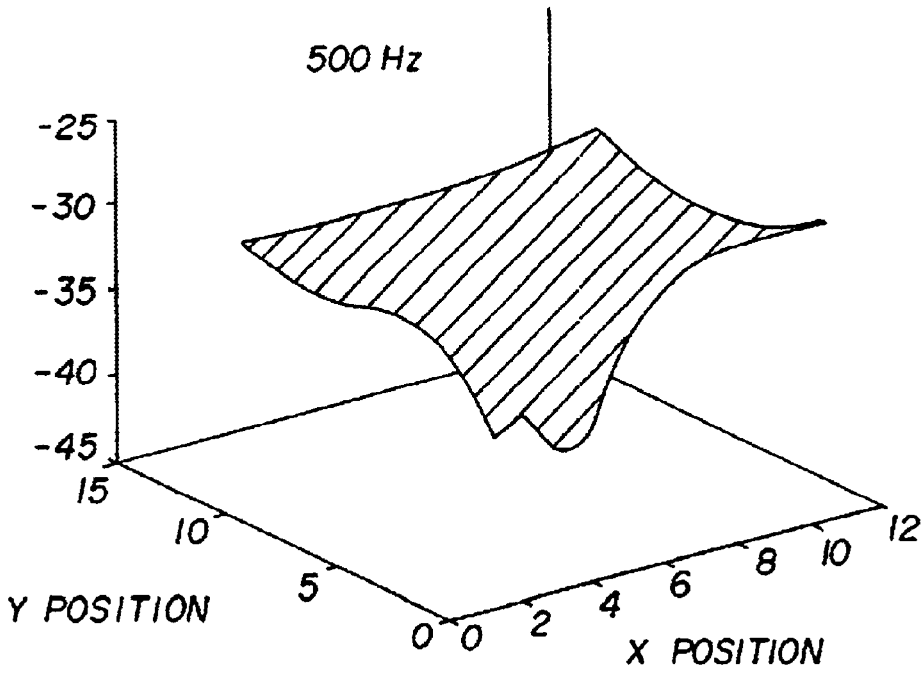
FIGS. 2A and 2B shows two three dimensional plots depicting the changes with frequency of the spatial areas of silence about error microphones for a given position away from the control speaker.
Figure 2B:
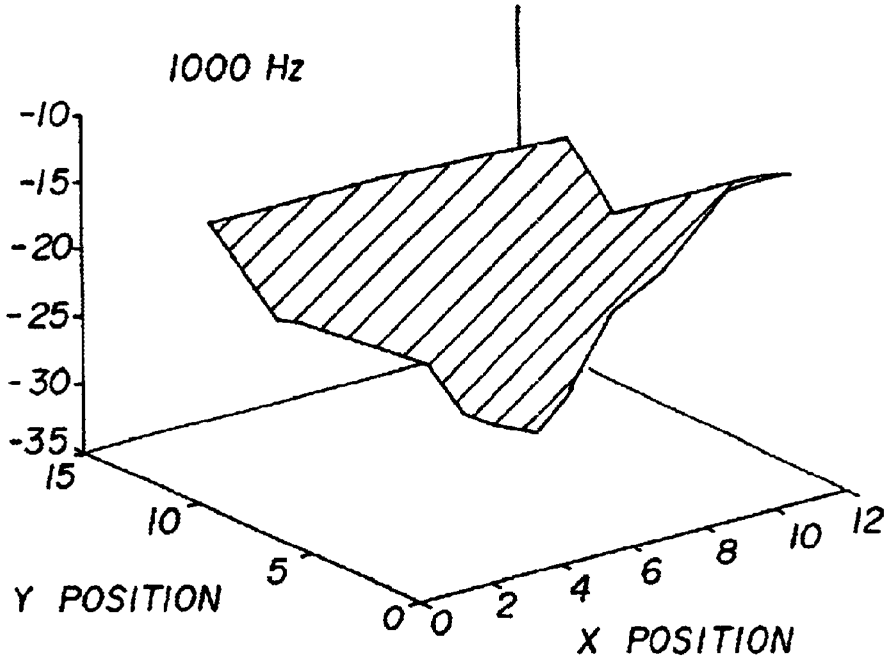
Figure 3:
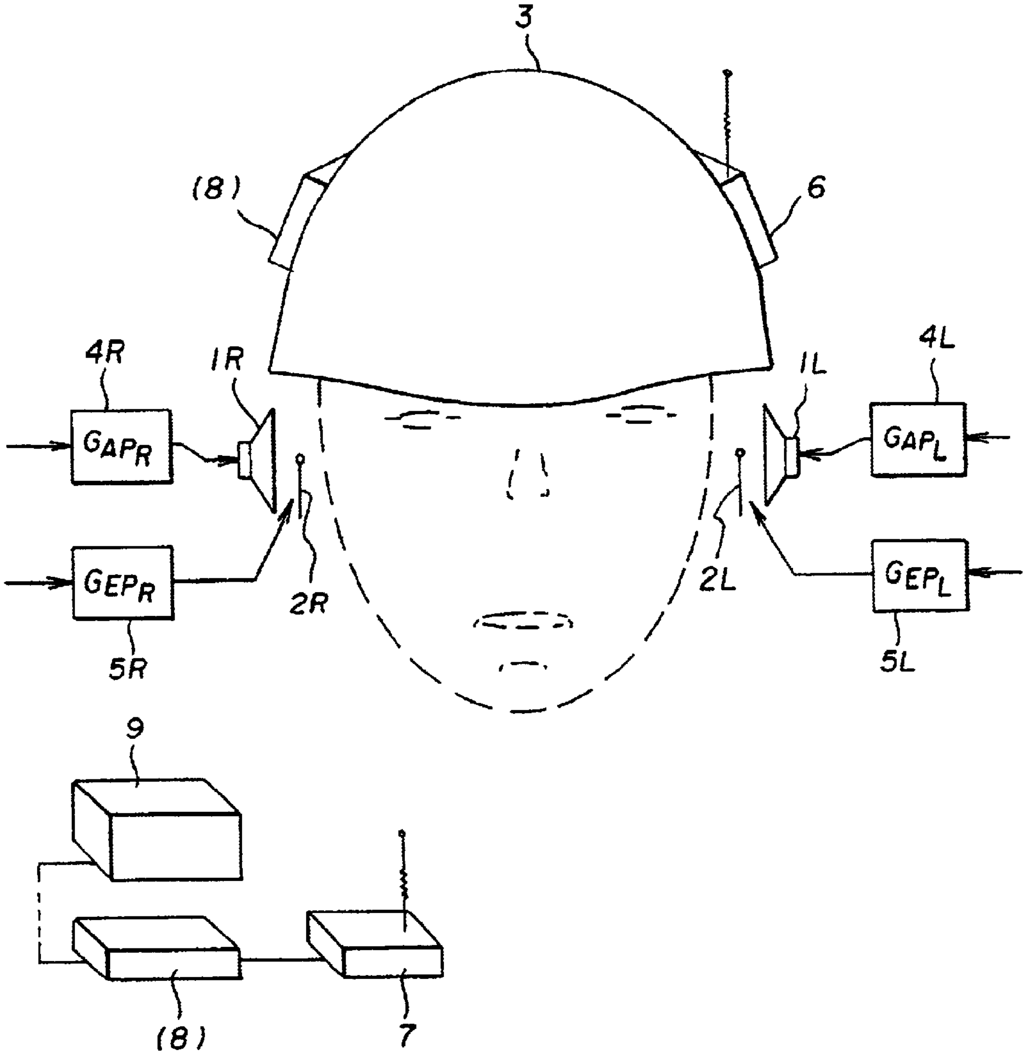
FIGS. 3 and 3*a* represent the adaptive personal ANR system depicted in only one of many possible embodiments, in this case a helmet adaptation and specific embodiments of the adaptable positioning system, respectively.

Referring to FIG. 3 the adaptable personal ANR system is shown consisting of two electroacoustic actuators 1R and 1L, a pair of acoustic-electric transducers 2R, 2L, a mounting apparatus and means for adjusting the relative and absolute positions of the actuators and transducers 4R, 4L, 5R and 5L.

As seen in FIG. 3, each of the right and left electric-acoustic actuators 1R and 1L are adjustably affixed to the mounting apparatus 3 by means GAP (4R and 4L) which permits movement of the actuator with respect to the user's ear and with respect to the mounting apparatus. This feature is included in order to allow various sized users to wear the apparatus comfortably and maximize the reduction of objectionable noise arriving at the user's eardrum. The actuators are mounted to 3 in a manner in which there is no portion of the actuator touching the users head but rather "floating" on the mount away from the user's ear. At no point during the operation will any portion of the actuator or transducer contact the user's head or ear thereby leaving normal communication and hearing acuity intact apart from any passive noise reduction measures. The headgear 3 has been designed with several degrees of freedom for the wearer in order to optimize performance with respect to the user's perception of sound. To facilitate this there is movement of the control speakers with respect to the wearer's ears (in and out, front and back), movement of the error microphone with respect to the wearer's ear canal and limited relative movement of the microphone with respect to the control speaker. The headgear will accommodate different size heads. The controller hardware and reference signal required by the feedforward controller can locate remotely (from the user) while the control speakers and error microphones can be located on the user. Communications between these devices requires two separate two-way channels, one each for receiving the control signal and one each for sending the microphone signals. Such an arrangement minimizes the "load" on the user insofar as hardware is concerned. Alternatively, the control hardware can be loaded on the user and requires a single one-way line wireless communication to the hardware on the user.

The size of the zone of silence around the microphone created by the control speaker is a function of frequency, decreasing in size with higher frequency. Depending on the characteristics of the noise field the user can adjust the position of the microphone with respect to his or her own hearing to maximize the sound reduction that is actually heard. No existing ANR headgear show this feature.

Several overall system structures or embodiments are realized in varying levels of wireless data communication and remote battery powered operation or also powered via a tethered line supplying power. FIG. 3 illustrates the first (and second) structures wherein the first utilizes a non-tethered wireless data transmission and receiver system one mounted to 3 mounting apparatus 6 and one remote data transmission and receiver system 7 which transmits two transducer signals from 2R and 2L and receives two actuator signals driving 2R and 2L wherein the digital signal processor and control hardware (8 located adjacent to 7 not mounted on 3) are also remote and not mounted to 3. The second embodiment removes 8 from the remote location adjacent to 7 and affixes it to the mounting apparatus 3 in that the only signal which will be transmitted is from the objectionable noise source to 7 in a wireless manner to 6 and received by 8. The digital signal processor in both embodiments 8 requires signals from 2R and 2L and 9 and provides signals for actuators 1R and 1L. The signal from the disturbing acoustic noise 9 is to be coherent with the acoustic disturbance arriving at each of the transducers 2R and 2L as mandated by the feedforward portion of the heteronomous control law now presented.

Figure 3A:
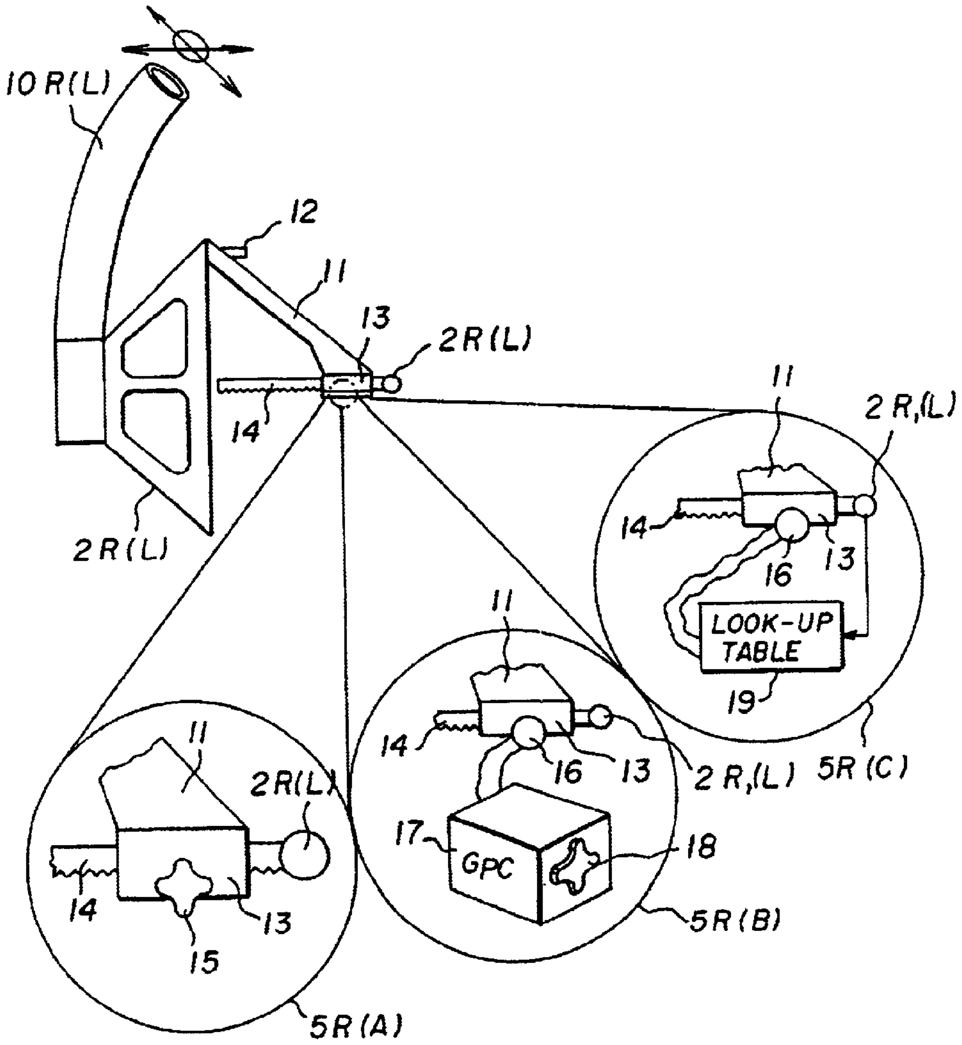

Each of the right and left side acoustic-electric transducers 2R (L) are adjustable mounted directly onto the electric-acoustic actuators 1R (L). The transfer function 5R (L) GEP represents the adaptable position of the error microphone which when 9 mounted directly to 1R (L) is affected by either a manual positioning system using a gear train which restrains the microphone to an amount of travel in which the electric-acoustic to acoustic-electric transfer function remains nominally unchanged or an automated motor driven system commanded by a manual input dial or a fully automated motor driven system which calculates the optimal position of the transducer 2R (L) with respect to the noise field, the position of the transducer relative to the actuator, and the position of the transducer relative to the eardrum. Referring to FIG. 3*a* these three embodiments are illustrated at 5 R (A, B and C) in the close-up views of the overall apparatus. The electro-acoustic actuator is adjustably mounted via 10R (L) including front, back, up, down, in, out, and rotationally with respect to the wearer in order to accommodate many sized heads and ear positions. The acoustic-electric transducer stator (mount 11) is adjustably affixed to 1R (L) via 12 (a set screw) which allows movement rotationally about screw 12 in the plane of the wearer's ear to ultimately adjust the position of the sensor 2R (L) given the user's desire for optimal noise reduction and comfort.

The rack and pinion system used for positioning the sensor in the sense that it is closer or farther from the wearer's ear canal consists of the housing 13, the rack 14, and the pinion gear internal to the housing which is driven and controlled in one of three possible manners detailed in 5R (A, B, and C). 5R (A) details the manual dial 15 used to rotate the pinion gear which drives the rack and positions the sensor 2R (L). This embodiment provides the user with direct control over the position of the microphone affording the possibility of maximum user-perceived noise reduction within the constraints of the control algorithm 5R (B) replaces the manual dial 15 with a very small DC motor 16 which instead drives the pinion of 5R (A) but may be more readily adjustable since the dial 18 can be located in a more ergonomically feasible location. Finally, the illustration in 5R (B) can be further modified as in 5R (C) to replace the user selectability with an algorithm which maximizes the field of silence surrounding the sensor depending on the sensor's location from the transducer 1R (L) and the general character of the noise field. For example, a predominantly low frequency noise field sensed by 2R (L) will result in 19 commanding the motor 16 to move the rack (and thus the sensor) to/from the transducer to maximize the silent zone around the microphone. The drawback of this approach is that no user interaction is facilitated and may result in a slightly less than optimal noise reduction perceived at the eardrum.

The user selectable embodiments of this apparatus SR (A and B) rely on loudness feedback from the user's perception of the noise field to be cancelled and are therefore optimal for reduction of loudness experienced by the user. Affixing 2R and 2L directly to 1R and 1L by aforementioned means GEP, adjustment relative to the actuator and the eardrum is affected based on the position of the actuator. Both embodiments require restricted movement of the transducer with respect to the actuator for reasons involving a stable system identification of the actuator to transducer transfer function as well as maintaining the location of the transducer within the radius of reverberation of the actuator thereby permitting a minimal power control force imparted by the actuator.

Figure 4:
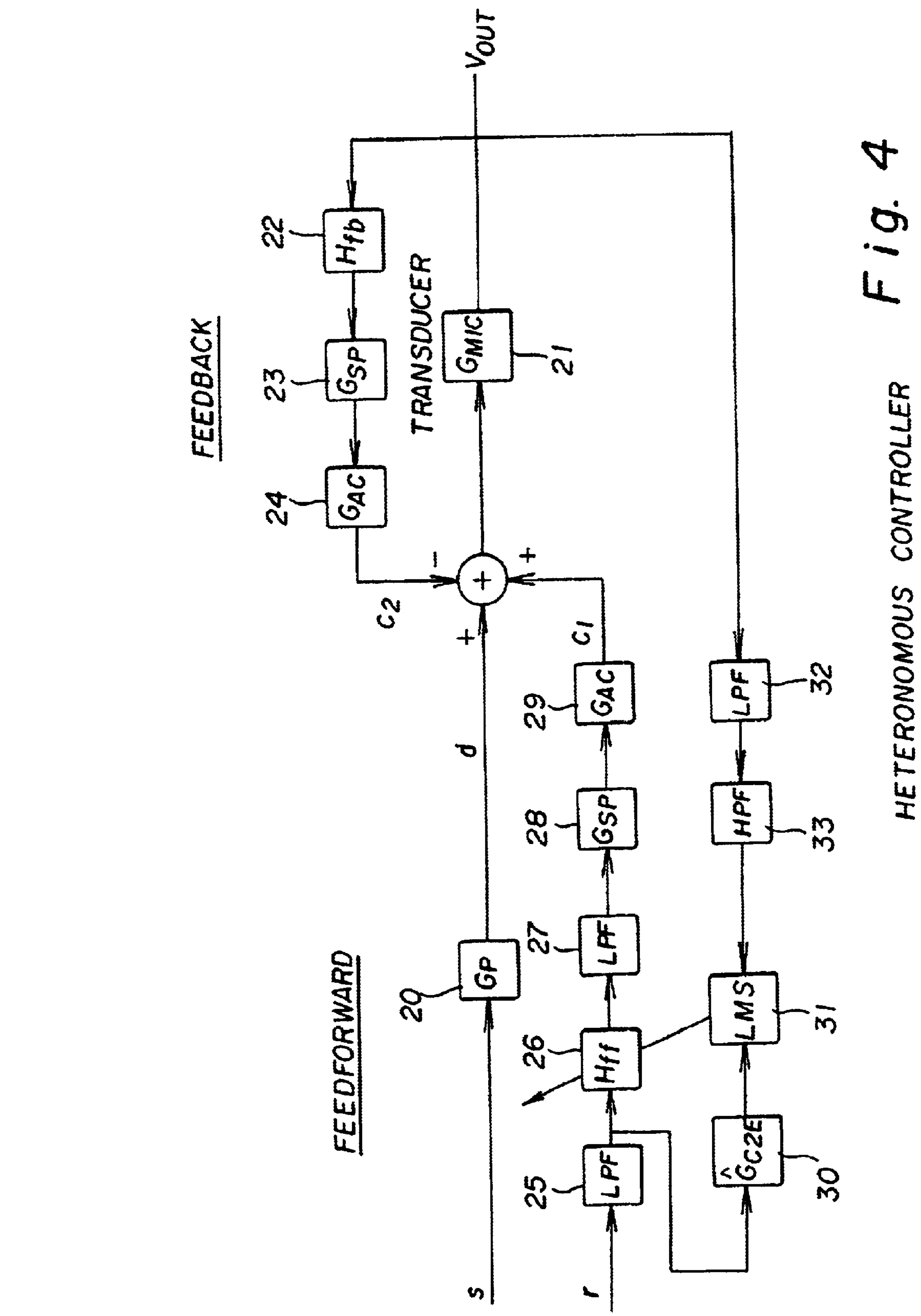
FIG. 4 is a block diagram showing the general structure for the heteronomous controller and signal paths used in attenuating the objectionable noise arriving at the user's ear canal.
Figure 5:
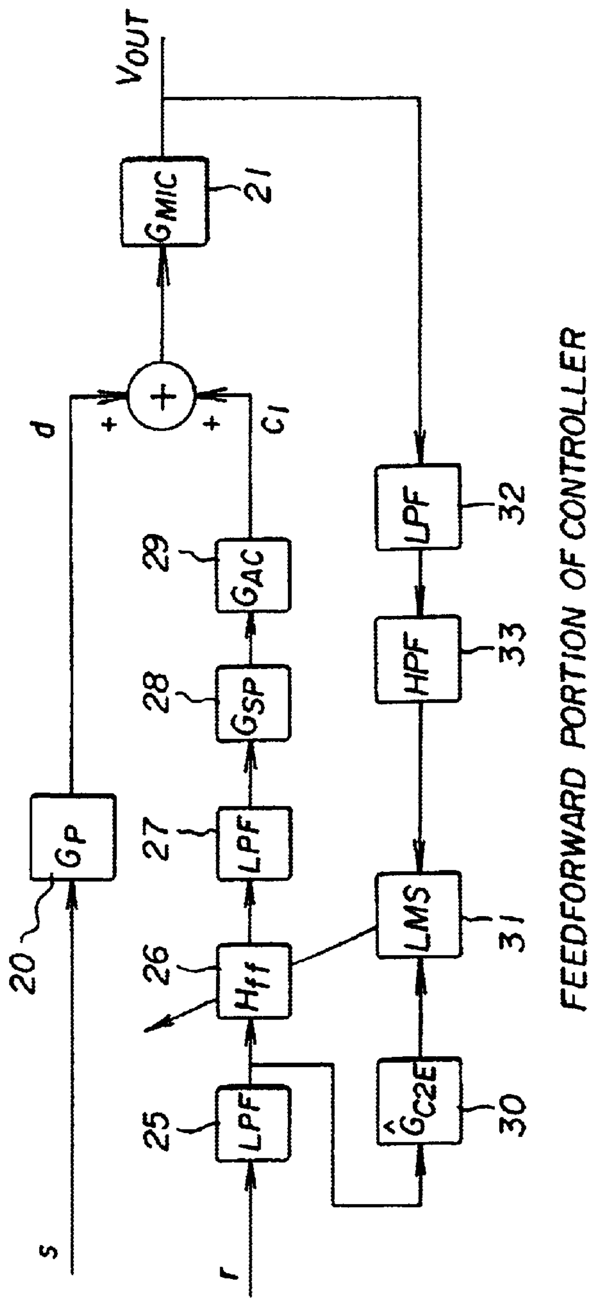
FIG. 5 is a block diagram showing only the feedforward portion of the heteronomous controller.
Figure 6:
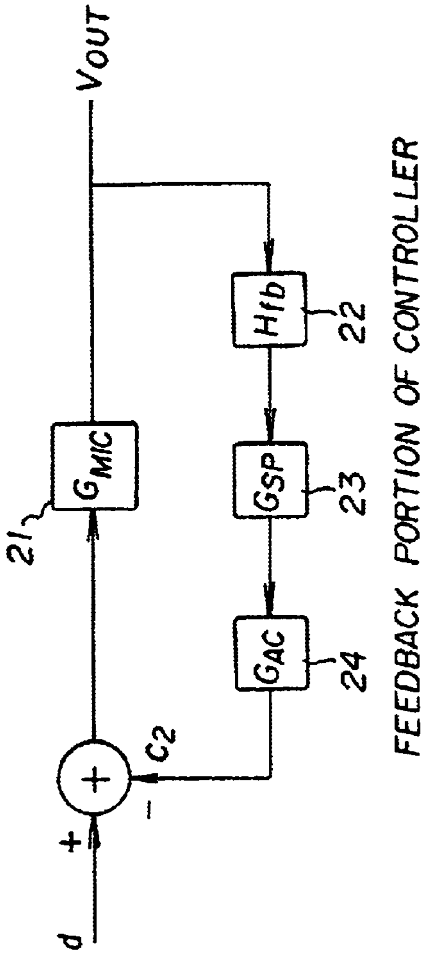
FIG. 6 is a block diagram showing only the feedback portion of the heteronomous controller from FIG. 1.

FIG. 4 represents the system architecture for the heteronomous controller resident on the digital signal processor 8 while FIGS. 5 and 6 extract the individual feedforward and feedback controller portions of the control system. FIG. 5 shows the adaptive feedforward controller portion of the heteronomous control system which utilizes either the conventional LMS algorithm or a modified version termed as the leaky LMS algorithm 31 which uses a tap delay line weight update equation preventing overflow in limited precision hardware platforms conforming to:

$$\hat{w}(n+1)=(1-\mu\alpha.)\ \hat{w}(n)+\mu V_{out}(n)r(n)$$

which updates the self designing FIR filter $H_{ff}$ 26 by using a filtered 30 input signal r and the transducer signal $V_{out}$ to create a controller which minimizes the mean square of the $V_{out}$ signal. The filtered input signal conforms to the common filtered-x algorithm for noise control where the input must be filtered by an estimate of the transducer function existing from the actuator output to the acoustic-electric transducer because the output of the controller itself does not act directly upon the disturbance d and thus must be taken into account before control commences. Since the acoustic-electric transducer is located and constrained to remain within the radius of reverberation of the control actuator, the transfer function estimate of the filtered-x algorithm does not significantly change with changing relative position and thus can be fixed and saved in the digital signal processor memory prior to control eliminating the need for continual update of the estimate. The transfer function is identified for all frequencies within the control bandwidth and thus is specified independent of the nature of the disturbance signal.

Proceeding through FIG. 5 the input r to the feedforward controller is first low pass filtered 25 for anti-aliasing purposes and used in the update of the weights 31 of the FIR filter as well as filtered by the adaptive feedforward transfer function $H_{ff}$ 26 whose output is smoothed using another low pass filter 27 whose output experiences the electric-acoustic transducer transfer function 28 and the acoustic path 29 traveling to the acoustic-electric transfer function which is also dynamically located via aforementioned means and is exposed to the objectionable noise d from some physical disturbance 20 originating from some source s wherein the input of the feedforward controller r is coherent with s. The output of the acoustic electric transducer 21 is conditioned to remove low and high frequency content beyond the controller bandwidth using both a low pass and high pass filter means 32 and 33.

Feedforward control typically does well when controlling tonal content and can generally eliminate the noise at the error microphone and maintain stability. Conversely, feedback control can effectively eliminate broadband sound up to 25 dB in some frequency ranges.

FIG. 6 shows the portion of the heteronomous controller which is considered to derive strictly from feedback control theory. The undesirable disturbance signal d is the same as which is shown in FIG. 4 and FIG. 5 for the feedforward controller and the acoustic-electric transfer function also receives sound pressure from the feedback control actuation force applied through 23 which is the same actuator as in the feedforward controller although labeled 28. The output signal from the acoustic-electric transducer 21 is used as the feedback signal for the compensation $H_{fb}$ 22 which is designed in order to perform a rejection of the disturbance noise thereby increasing the gain of 22 while maintaining appropriate stability margins which will minimize the sensitivity function of the feedback system. The output of the controller drives the control actuator which is also being driven by the feedforward controller thus 28 and 23 are the same actuator in the heteronomous controller for a single side, right or left.

Figure 7:
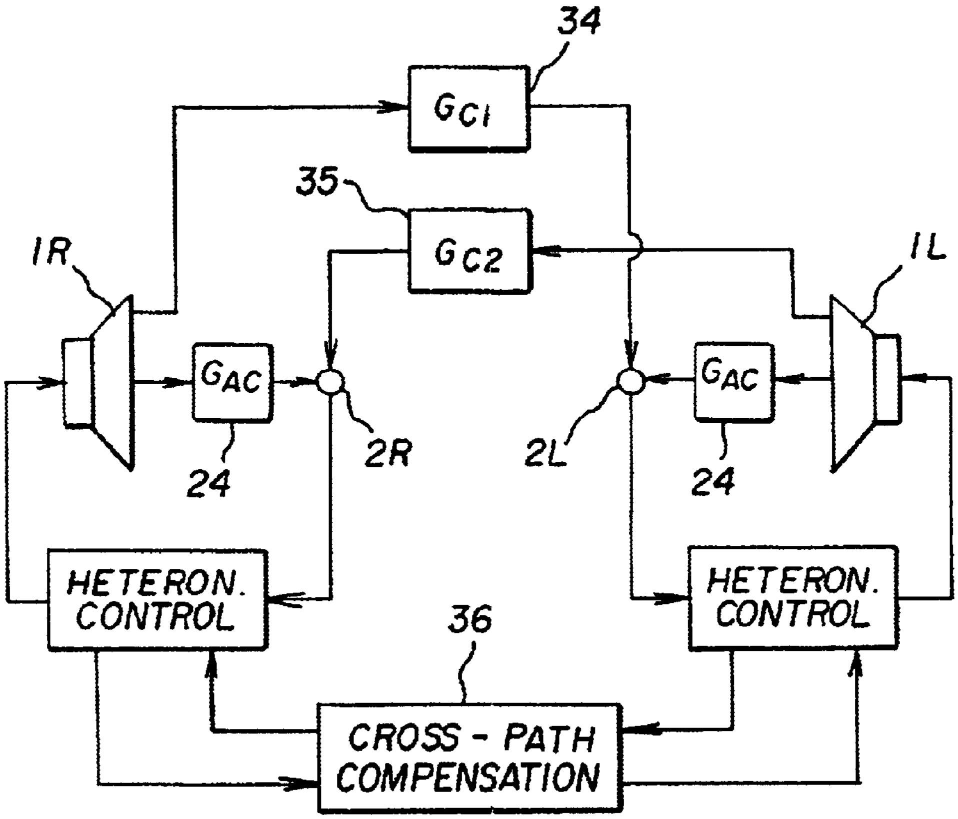
FIG. 7 is a block diagram schematic showing the existence of cross paths between the left and right side transducers and actuators.

FIG. 7 illustrates the paths which exist (34 and 35) between the right side actuator 1R, the left side transducer 2L as well as between the left side actuator 1L and the right side transducer 2R. In performing both the feedforward and feedback control actions these paths are taken into account with respect to each other 36 so as to prevent positive feedback and instabilities in the overall system.

Figure 9:
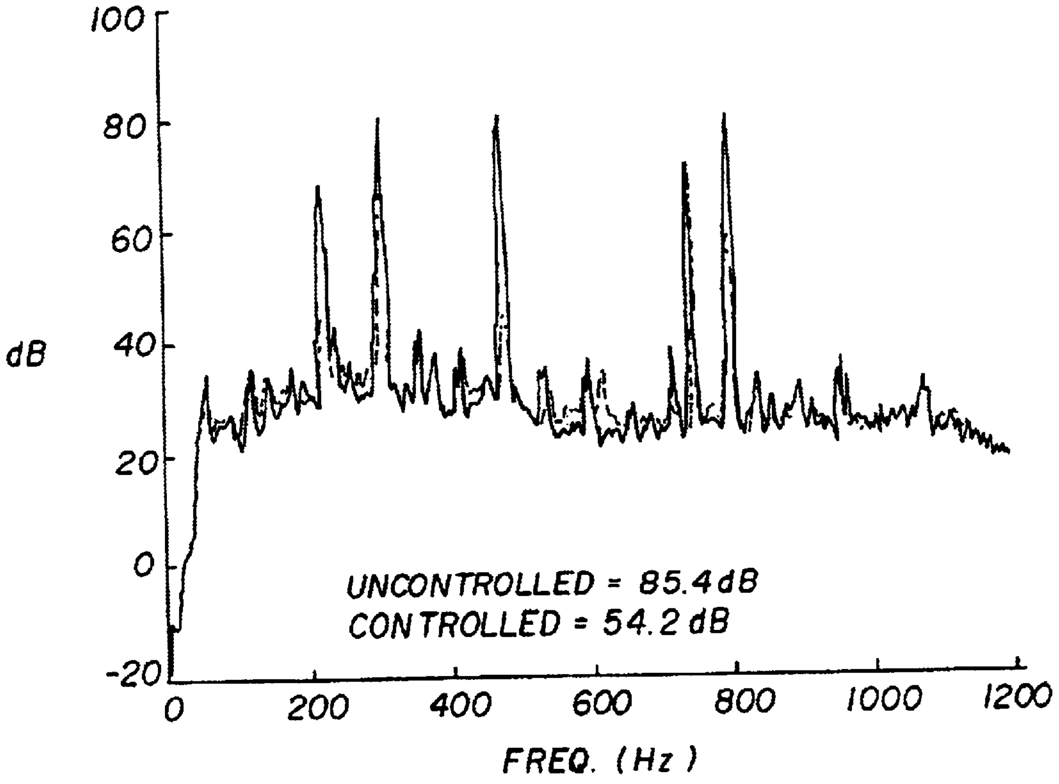
FIG. 9 is a plot illustrating the amount of reduction achieved at the left ear using only the feedforward portion of the heteronomous controller for a five tonal noise field.

To summarize thus far, the heteronomous controller is used to reduce the objectionable sound power reaching the user's ears. The central summing junction represents the overall sound power incident on the acoustic-electric transducer from the heteronomous controller which includes both the feedback and feedforward control algorithms as well as the undesirable sound power d reaching the user's ears and the cross path terms from 34 and 35. It is emphasized that control actuation and acoustic paths shown as 23 and 24 are also represented as the control actuator and acoustic paths used in the feedforward portion of the control scheme therefore in effect the output signal of 22 and the output signal of 27 are linearly combined prior to driving the electric-acoustic actuator but are shown separately in order to clarify the two control schemes. The feedforward controller is capable of achieving tonal control (shown in FIG. 9) with extreme authority (up to 50 dB) due to its robustly stable design but becomes increasingly incapable for broadband noise fields having large frequency ranges of control which in turn requires large filter sizes and computational overhead. Feedback control offers less overall reduction but provides broadband noise control (FIG. 10) for wide frequency ranges. Summing the control forces from each of these methods results in a robustly stable controller capable of suppressing very colorful noise fields including high amplitude tonals as well as moderate broadband noise fields. FIG. 11 shows this arrangement.

Figure 8:
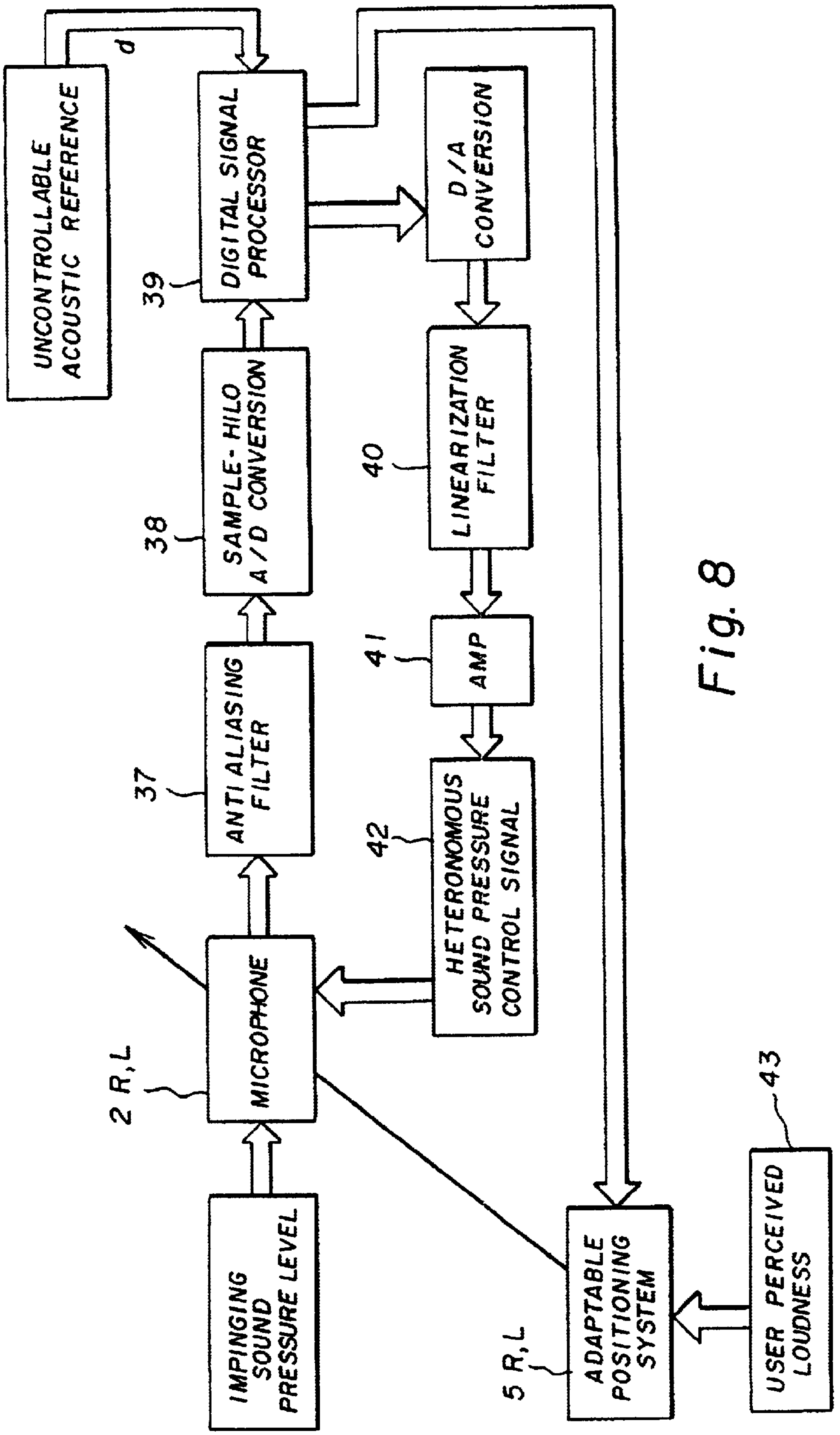
FIG. 8 is a block diagram which shows the individual components of the heteronomous, adaptable positioning ANR system.

FIG. 8 illustrates two embodiments of the controller design. An impinging sound pressure level is transduced by a microphone subject to a control input from the adaptable positioning system. The adaptable positioning system is realized using apriori information about the ANR components and information from the DSP processor in regards to the spectral content of the sound field. The microphone signal goes through the data acquisition components (anti-aliasing filter, sample-hold circuit, and analog-to-digital converter.) and is processed by the DSP. A feedforward and feedback control signal exits the DSP block. The feedforward controller is a digital filter by design can be realized in one of two possible ways. The first is via analog hardware represented by a fixed design operational amplifier circuit or designed in conjunction with the feedforward controller manifested as a fixed design digital IIR filter operating at the same sample rate as the feedforward controller. FIG. 8 illustrates the digital implementation.

Again referring to FIG. 8 the heteronomous control effect is evidenced in the acoustic-electric transducer output $V_{OUT}$ which can be shown to consist of a unique combination of compensation means described by $$V_{out}=G_{mic}/1+G_{mic}G_{ac}G_{sp}H_{fb}d+G_{mic}G_{ac}G_{sp}H_{ff}/1+G_{mic}G_{ac}G_{sp}H_{fb}r$$

Consequently, the heteronomous ANR performance can be considered as an adaptive compensation of the residual signal created by the feedback controller, as identified originally. A corresponding reduction in the spectral norm of the cross-correlation matrix between the reference input signal r and the error signal $V_{OUT}$ results in a significant advantage for the convergence characteristics of the adaptive portion as compared to prior art. Stability of the converged heteronomous ANR system is determined solely by the Hfb design.

The user of the instant invention can determine whether he wished to employ the feedback only, adaptive feedforward only or the combined system for reduction of both tonals and broadbands.

Figure 10:
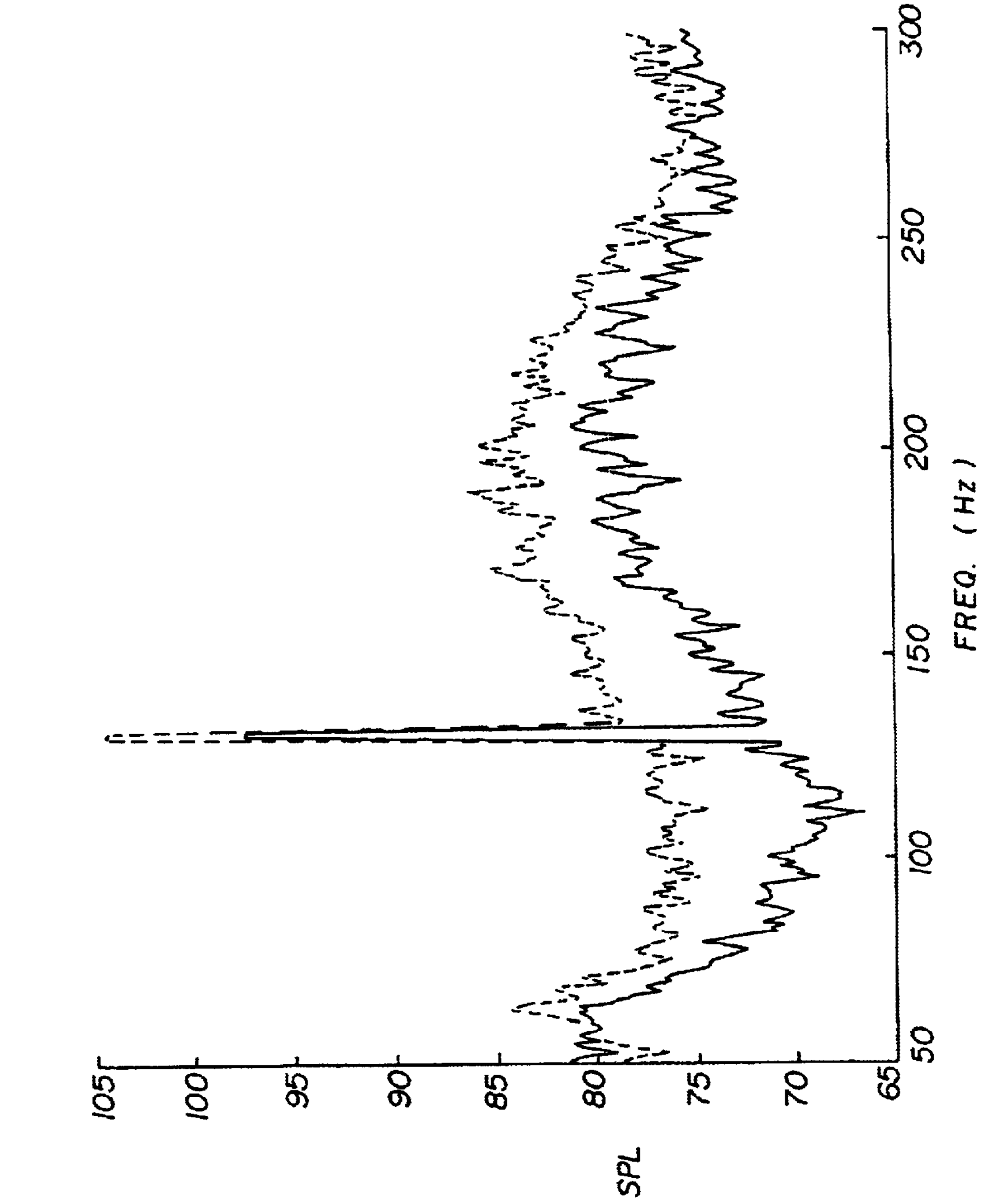
FIG. 10 illustrates the control exercised by the feedback portion of the heteronomous system for a broadband noise field.
Figure 11:
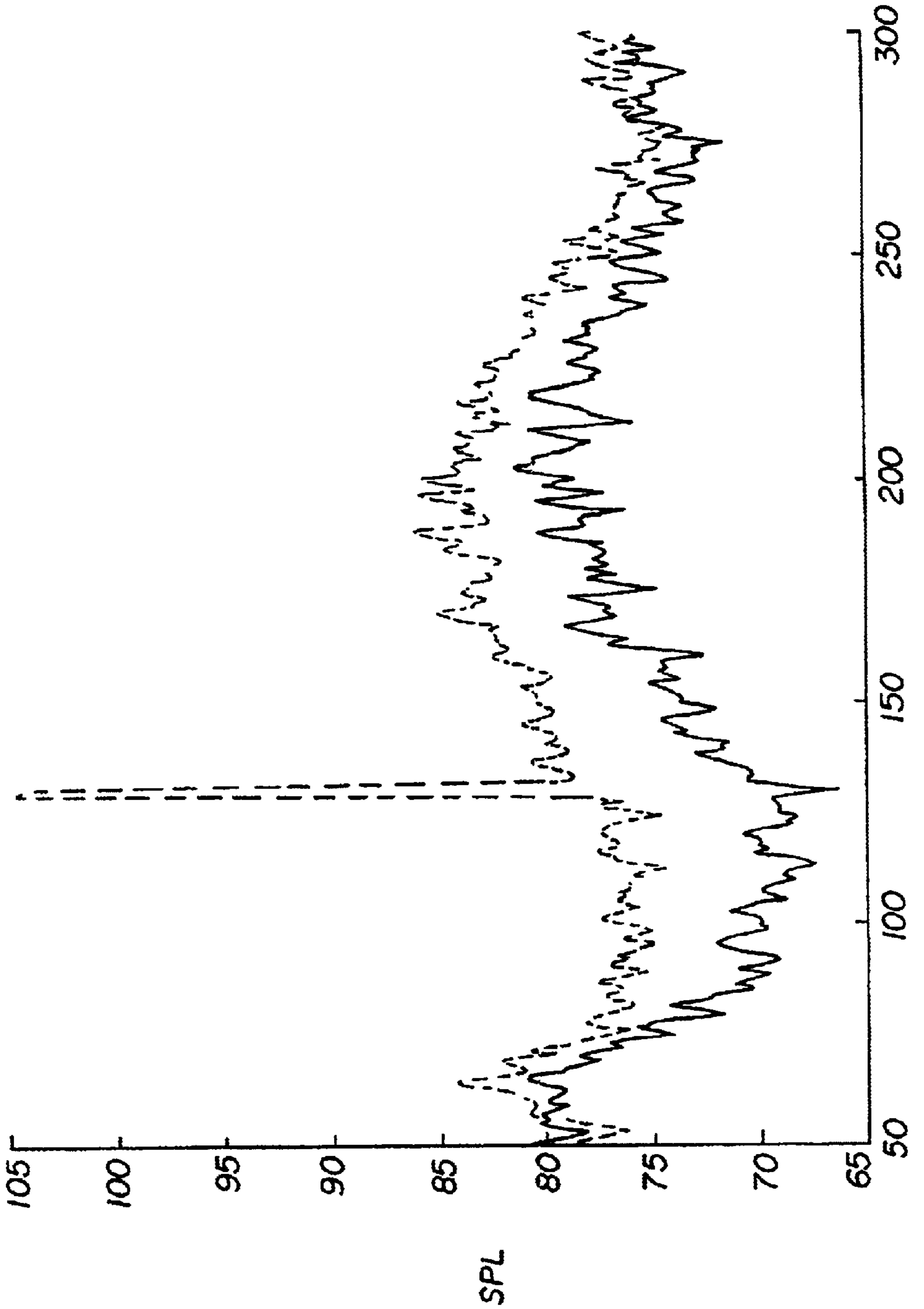
FIG. 11 illustrates the control achieved by the heteronomous controller on a noise field containing both broadband and tonal content.
Figure 12:
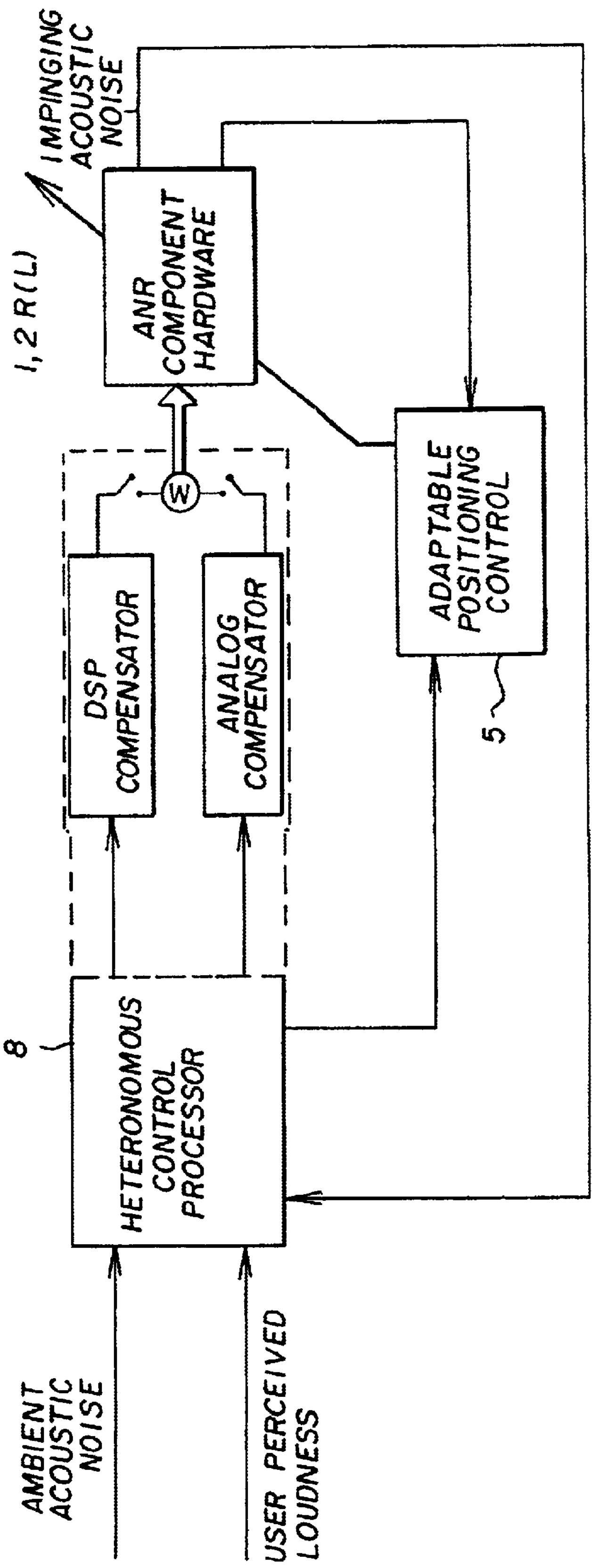
FIG. 12 is a block diagram showing the overall ANR system.

FIG. 10 shows the SPL versus frequency plot using feedback only in the headset system while FIG. 11 shows the SPL versus frequency plot for the heteronomous operation of headset system. FIG. 12 shows an overall block diagram view of the device showing the various inputs, components and interaction there between. Note that the heteronomous control processor feeds the DSP and Analog compensators which produce output to the ANR component hardware. Feedback from hardware flows back to the heteronomous control processor which compares it with an ambient acoustic noise input as well as a user perceived loudness input. The user adjusts the adaptable positioning control which optimizes the system to the user.

The above recital of the operation of the system can be enhanced by a review of the following articles: “Active Control of Sound and Vibration”, by C. R. Fuller and A. R. vonFlotow, IEEE Control Systems, December 1995, pp 9–19, “A Hybrid Structural Control Approach for Narrowband and Impulsive Disturbance Rejection”, by W. R. Saunders, H. H. Robertshaw and R. A. Burdisso, Noise Control Engineering Journal, Special Issue on Active Noise Control, Vol. 44, No. 1, January–Febuary, 1996; and “Active Noise Control Systems: Designing for the Auditory System”, by W. R. Saunders and M. A. Vaudrey, Proceedings of Noise-Con 96, Bellevue, Wash., September 1996. Each of these articles is incorporated herein by reference.

Having described the invention it is readily apparent that many changes and modifications thereto may be made by those of ordinary skill in the acoustic arts without departing from the scope of the appended claims.

What is claimed is:

1. An improved active noise cancellation headset, said headset comprising:

a headgear means for placement atop a user’s head;

at least one electro-acoustic transducer means mounted on said headgear means;

at least one acoustic-electro sensing means mounted on said headgear means adjacent to said electro-acoustic means, wherein said electro acoustic means and said acoustic-electro means are adjustable in relation to one another and user’s ears within a designated range, the area containing said electro-acoustic means and said acoustic-electro means defining a zone adjacent to at least one of the user’s ears;

attenuation control means of heteronomous design connected to said electro acoustic means and to said acoustic-electro means and adapted to attenuate selected sound frequencies in a sound field within said zone; and whereby said headset is adapted to cancel designated frequencies within said zone to create an area of silence or relative silence to the at least one of a user’s ears.

2. The headset of claim 1 wherein said attenuation control means includes an automatic mechanism for continually adjusting said electro-acoustic and said acoustic-electro means in relation to one another.

3. The headset as in claim 1 wherein said heteronomous attenuation control means comprises, a feedforward control means adapted to attenuate designated tonal sounds within said zone, and a feedback control means adapted to attenuate designated broadband sounds within said zone.

4. The headset of claim 3 wherein said heteronomous attenuation control means further comprises a switch means adapted to permit activation of the feedforward control means without activating the feedback control means, activation of the feedback control means without activating the feedforward control means, and activation of both the feedback control means and the feedforward control means simultaneously.

* * * * *